US00PP30866P2

(12) United States Plant Patent
Verhoef

(10) Patent No.: US PP30,866 P2
(45) Date of Patent: Sep. 3, 2019

(54) ***WEIGELA* PLANT NAMED 'VERWOF 1'**

(50) Latin Name: *Weigela florida*
Varietal Denomination: Verwof 1

(71) Applicant: Gijsbertus Verhoef, Hazerswoude-Dorp (NL)

(72) Inventor: Gijsbertus Verhoef, Hazerswoude-Dorp (NL)

( * ) Notice: Subject to any disclaimer, the term of this patent is extended or adjusted under 35 U.S.C. 154(b) by 0 days.

(21) Appl. No.: 15/732,495

(22) Filed: Nov. 20, 2017

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226, 263.1
CPC ..... A01H 5/02; A01H 5/0272; A01H 5/00; A01H 6/56; A01H 6/00
See application file for complete search history.

(56) References Cited

PUBLICATIONS

Farwest 2017 New Varieties Showcase, retrieved on Oct. 17, 2018, retrieved from the Internet at https://farwestshow.com/new-varieties-showcase-2017/, pp. 1 and 26. (Year: 2017).*

Gebeshuber. Vancouver Sun: Hot New Plants for 2017, Vanbelle (Nov. 21, 2016), retrieved on Oct. 17, 2018, retrieved from the Internet at https://vanbelle.com/news/vancouver-sun-hot-new-plants-for-2017/, 4 pp. (Year: 2016).*

Whysall. In the Garden: Hot new plants in the pipeline for 2017, Vancouver Sun (Nov. 18, 2016), retrieved on Oct. 17, 2018, retrieved from the Internet at https://vancouversun.com/homes/gardening/in-the-garden-hot-new-plants-in-the-pipeline-for-2017, 8 pp. (Year: 2016).*

Connon Nurseries Inventory Availability 2017, retrieved on Feb. 12, 2019, retrieved from the Internet at https://connon.ca/wp-content/uploads/2017/08/Inventory-Availability-Report.pdf, pp. 1 an 64. (Year: 2017).*

Vanbelle RocketLiners Youngplants Web Availability List 2017, retrieved on Feb. 12, 2019, retrieved from the Internet at https://docplayer.net/58912057-Rocketliners-availability-list.html, 11 pp. (Year: 2017).*

Van Belle Nursery Supplement—New Plant Pavilion, Nursery Management 2017, retrieved on Feb. 12, 2019, retrieved from the Internet at https://www.nurserymag.com/article/van-belle-nursery-february-2017/, 6 pp. (Year: 2017).*

* cited by examiner

*Primary Examiner* — June Hwu
(74) *Attorney, Agent, or Firm* — Penny J. Aguirre

(57) ABSTRACT

A new cultivar of *Weigela florida*, 'Verwof 1', characterized by its compact plant habit, its flower buds that are red in color and flowers that are purple-pink in color, its summer foliage that is green with a strong orange to bronze tinge and its autumn foliage that is burgundy red to crimson red in color.

3 Drawing Sheets

Botanical classification: *Weigela florida.*
Variety denomination: 'Verwof 1'.

BACKGROUND OF THE INVENTION

The present invention relates to a new and distinct cultivar of *Weigela* and will be referred to hereafter by its cultivar name, 'Verwof 1'. 'Verwof 1' represents a new cultivar of *Weigela*, a deciduous shrub grown for landscape use.

The new cultivar is the result of a controlled breeding program conducted by the Inventor in Hazerswoude-Dorp, The Netherlands. The objective of the program was to develop a new cultivar of *Weigela* with a compact plant habit and desirable foliage coloration and flowering habit.

The new cultivar of *Weigela* arose from a breeding program conducted by the Inventor in Hazerswoude-Dorp, The Netherlands. 'Verwof 1' originated as a seedling that arose from seed planted from open pollination of *Weigela* 'Wings of Fire' (U.S. Plant Pat. No. 21,920) in May 2012. 'Verwof 1' was selected as a single unique plant in summer of 2013 from amongst the resulting seedlings.

Asexual propagation of the new cultivar was first accomplished by softwood stem cuttings by the Inventor in summer of 2013 in Hazerswoude-Dorp, The Netherlands.

Asexual propagation by softwood stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Verwof 1' as a unique cultivar of *Weigela.*

1. 'Verwof 1' exhibits a compact plant habit.
2. 'Verwof 1' exhibits flower buds that are red in color and flowers that are purple-pink in color.
3. 'Verwof 1' exhibits summer foliage that is green with a strong orange to bronze tinge.
4. 'Verwof 1' exhibits autumn foliage that is burgundy red to crimson red in color.

The seed parent of 'Verwof 1', 'Wings of Fire', differs from 'Verwof 1' in having a much taller plant height with longer branches, a less compact plant habit, and in producing less flowers. 'Verwof 1' can also be compared to the *Weigela florida* cultivar 'Verweig' (U.S. Plant Pat. No. 16,824). 'Verweig' is similar to 'Verwof 1' in having a compact plant habit. 'Verweig' differs from 'Verwof 1' in having summer foliage that is bronze green with creamy margins, no autumn coloration and flowers that are light purple-pink in color.

BRIEF DESCRIPTION OF THE DRAWINGS

The accompanying colored photographs illustrates the overall appearance and distinct characteristics of the new *Weigela*. The plant in FIG. 1, FIG. 2

Figure 1:
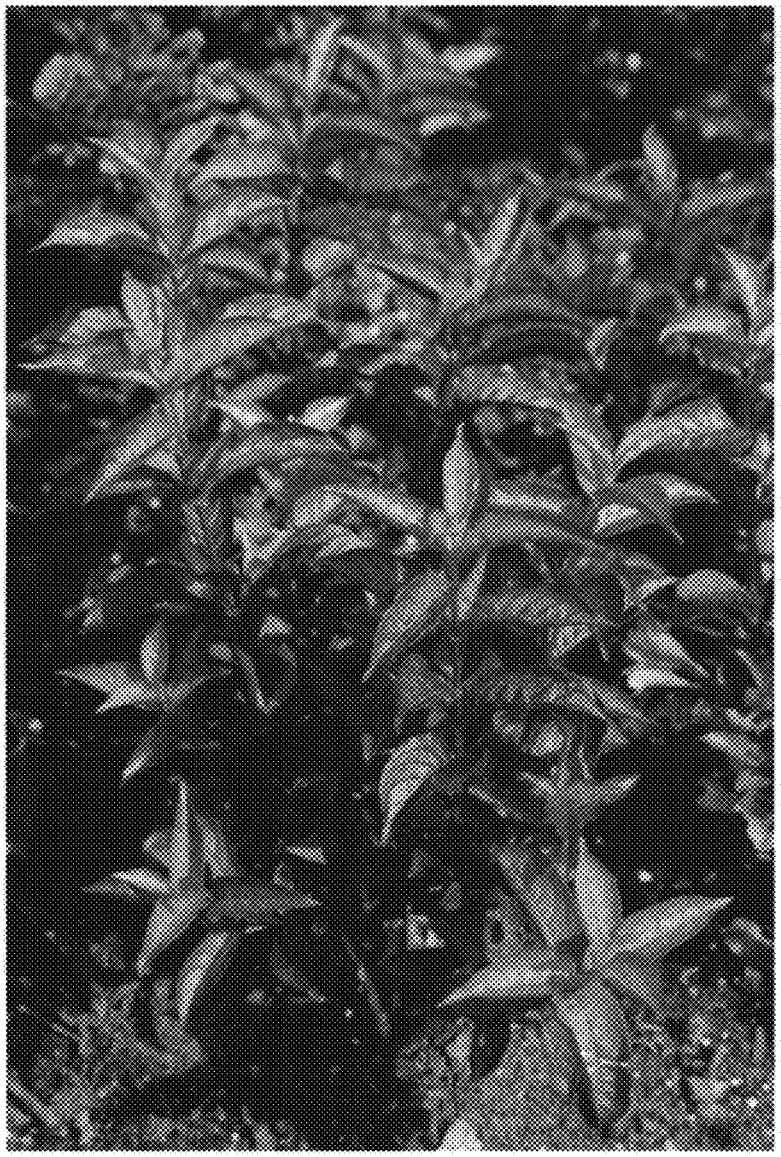

The photograph in FIG. 1 provides an overall view of the growth habit of 'Verwof 1'.

Figure 2:
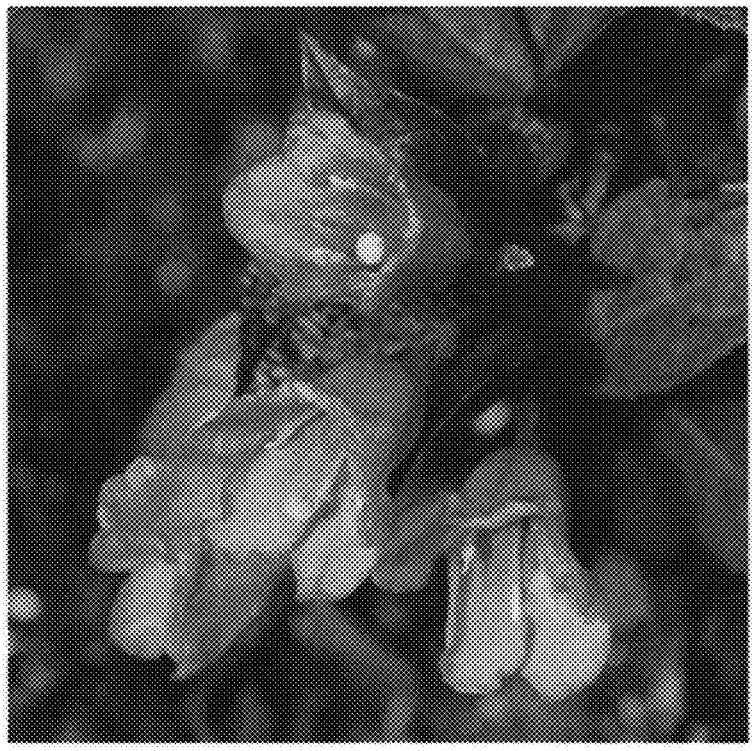

The photograph in FIG. 2 provides a close-up view of the flowers of 'Verwof 1'.

Figure 3:
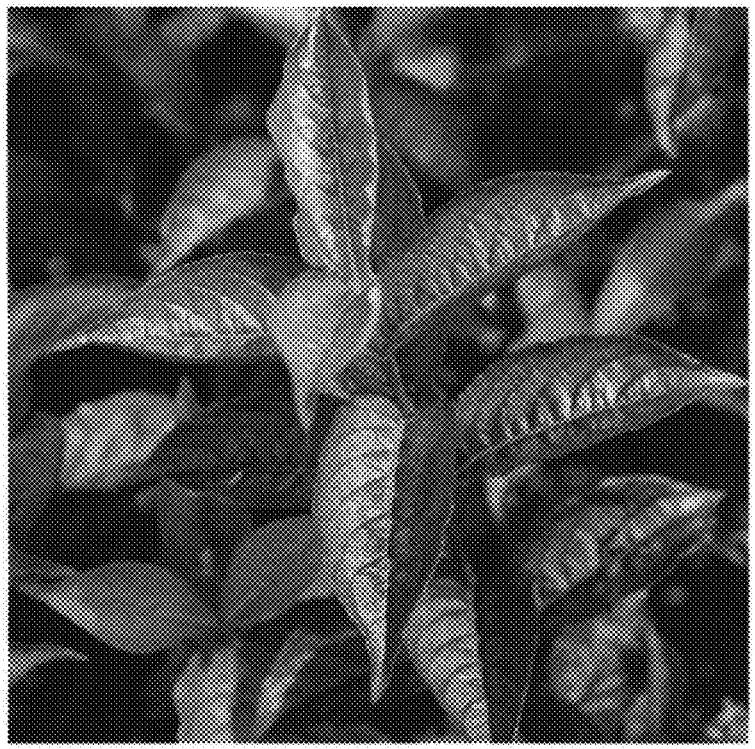
FIG. 3 is 17-months in age and grown outdoors in a trial field Hazerswoude-Dorp, The Netherlands.

The photograph in FIG. 3 provides a close-up view of the foliage of 'Verwof 1'.

Figure 4:
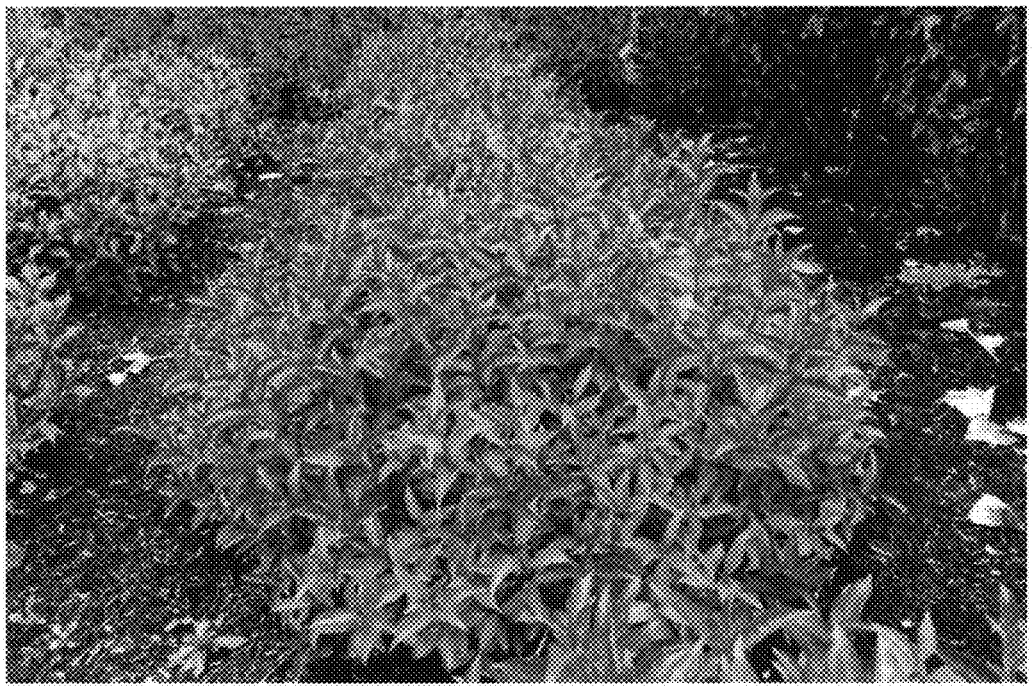

The photograph in FIG. 4 provides a close-up view of the fall foliage. 'Verwof 1' and was taken of a plant 2 years in age as grown in a trial field in Abbotsford, BC, Canada.

The colors in the photographs may differ slightly from the color values cited in the detailed botanical description, which accurately describe the colors of the new *Weigela*.

DETAILED BOTANICAL DESCRIPTION

The following is a detailed description of 17 month-old plants of the new cultivar as grown in a trial field in Hazerswoude, The Netherlands. Phenotypic differences may be observed with variations in environmental, climatic, and cultural conditions. The color determination is in accordance with The 2015 R.H.S. Colour Chart of The Royal Horticultural Society, London, England, except where general color terms of ordinary dictionary significance are used.

General description:

*Blooming period.*—Blooms from spring (May) and August and September in The Netherlands.

*Plant type.*—Deciduous shrub.

*Plant habit.*—Upright and broadly ovate, freely branched.

*Plant size.*—In the landscape; an average of 37.9 cm in height (soil level to top of foliar plane), 22.4 cm in height (soil level to top of floral plane) and 35 cm in diameter, eventually a mature plant will be 40 cm in height and width.

*Hardiness.*—At least in U.S.D.A. Zones 5 to 9.

*Diseases and pests.*—No susceptibility to resistance to diseases or pests has been observed.

*Root description.*—Fibrous, moderately dense.

*Propagation.*—Softwood stem cuttings.

*Root initiation.*—An average of 2 months.

*Root development.*—An average of 4 months to produce a young rooted plant.

*Growth rate.*—Moderately vigorous.

Branch description:

*Branch shape.*—Slightly quadrangular.

*Branch color.*—New growth; 179B, mature wood; bark; 199B to N199B.

*Branch size.*—An average of 28.7 cm in length and 5 mm in diameter.

*Branch surface.*—Moderately glossy, sparsely covered with short strigose hairs; average of 0.3 cm in length, too small to measure color.

*Branch aspect.*—Upright to outward at an average angle of 40°.

*Branch quantity.*—Average of 2 main branches, 8 lateral branches.

*Internode length.*—2.6 cm.

Foliage description:

*Leaf shape.*—Ovate to elliptic.

*Leaf division.*—Simple.

*Leaf base.*—Obtuse.

*Leaf apex.*—Apiculate.

*Leaf fragrance.*—None.

*Leaf aspect.*—Held in an average angle of 40° to lateral branch.

*Leaf venation.*—Pinnate, color upper surface; 162B on new growth and 179A to 179B on mature growth, color lower surface; 180A to 180B.

*Leaf margins.*—Serrate.

*Leaf arrangement.*—Opposite.

*Leaf attachment.*—Petiolate.

*Leaf surface.*—Both surfaces are smooth, glabrous and slightly glossy, rugose, veins are moderately covered with pubescence, average of 0.2 to 0.5 mm in length and 155A to 156D in color.

*Leaf size.*—An average of 6.1 cm in length and 3.4 cm in width.

*Leaf quantity.*—An average of 24 (12 pairs) per lateral branch.

*Leaf color.*—Young upper surface; 146A, finely edged and tipped with 183A, young lower surface; 146B, fading towards the margins and top to 176A, mature upper surface; 146A, very strongly tinged 200A, mature lower surface; 146D, fading towards the margins and top to 177A, young and mature upper and lower surface fall color; bottom section of plant 144C, mid-section of plant 144C becoming flushed with a blend of 171B, 44A and 183A, top section of plant turns to a blend 44A and 183A.

*Petioles.*—Average of 4 mm in length, 2.5 mm in width, flattened, upper surface color 151A, margins 180B, lower surface color 180A, strong, both surfaces are smooth and slightly glossy with margins covered with short soft hairs an average of 0.5 mm in length and 156D in color.

*Stipules.*—None.

Inflorescence description:

*Inflorescence type.*—Solitary, in pairs, or in small clusters at terminus and leaf axils.

*Inflorescence size.*—4.7 cm in height (including peduncle), 4.9 cm in diameter.

*Flower buds.*—Oblanceolate in shape, an average of 2.4 cm in depth and 7 mm in diameter, 184C in color, smooth, glabrous and matte surface, sparsely covered with very short hairs an average of 0.2 mm in length, too small to measure color.

*Flower fragrance.*—None.

*Lastingness of flowers.*—About 12 days, self-cleaning.

*Flower aspect.*—Outward to slightly upright.

*Flower quantity.*—An average 5 per inflorescence, 30 buds and flowers per plant.

*Flower type.*—Tubular.

*Flower size.*—Average of 1.8 cm in height, 2.2 cm in diameter, 3 cm in depth, throat; 7 mm in diameter, tube; 2.2 cm in length, 8 mm in diameter.

*Peduncles.*—Average of 2.1 cm in length and 1.5 mm in diameter, held straight on top of lateral branch, rounded, moderate strength, smooth, glabrous and moderately glossy surface, 178B in color.

*Pedicels.*—Average of 2 mm in length and 1 mm in diameter, held in an angle of 25° to peduncle, rounded, moderate strength, smooth, glabrous and slightly glossy surface, 175A in color.

*Calyx.*—Rotate in shape, an average of 5 mm in depth and 2.5 mm in width.

*Sepals.*—5, rotate, linear in shape, narrowly acute apex, cuneate base, lower 50% fused, entire margin, an average of 5 mm in length and 0.8 mm in width, upper and lower surface is smooth, glabrous and dull, color; when opening upper and lower surface 181C, tinged with 146D at the tip, when fully open upper and lower surface 180B.

*Petals.*—5, lower 75% fused into tube, spathulate in shape, margin entire on free portion, apex obtuse, an average of 3 cm in length, 9 mm in width, color; upper and lower surface glabrous and moderately velvety, color; when opening upper surface 185B, when opening lower surface 184C, fully open upper surface; 184D, fully open lower surface 185B, throat color; 184D, narrow blotch present on one of the petals 8D and 34B in color, tube color; outer surface 184D, inner surface between 185A and 185B.

Reproductive organs:

*Gynoecium.*—Pistil; 1, average of 2.9 cm in length, style; average of 2.8 cm in length, and 65D in color, fading towards the proximal end to 63C in color, stigma; club-shaped, 1 mm in length, 2 mm in diameter, N155A in color, ovary; 178B.

*Androecium.*—Stamens; 5, filaments; 186C in color and an average of 1 cm in length, implanted in petals, anthers; 8D in color, an average of 4 mm in length, 0.5 mm in width, narrowly oblong in shape, pollen; low in quantity and 11D in color.

*Fruit and seed.*—No fruit or seed production has been observed to date.

It is claimed:

1. A new and distinct cultivar of *Weigela* plant named 'Verwof 1' as herein illustrated and described.

* * * * *